United States Patent [19]

Iwasaki et al.

[11] Patent Number: 4,879,412

[45] Date of Patent: Nov. 7, 1989

[54] PURIFICATION PROCESS OF METHACRYLIC ACID

[75] Inventors: Kozo Iwasaki, Yokohama; Morimasa Kuragano, Osaka; Minoru Koshibe, Osaka; Yoshihiro Sezaki, Osaka; Katsuji Yoguchi, Kitakanbara; Yoshio Koyama, Osaka, all of Japan

[73] Assignees: Mitsui Toatsu Chemicals, Inc.; Kyowa Gas Chemical Industry Co., Ltd., both of Toyko, Japan

[21] Appl. No.: 835,737

[22] Filed: Mar. 3, 1986

[30] Foreign Application Priority Data

Mar. 14, 1985 [JP] Japan .................................. 60-49248
Apr. 10, 1985 [JP] Japan .................................. 60-74351
Jun. 25, 1985 [JP] Japan ................................ 60-136882

[51] Int. Cl.$^4$ ............................................. C07C 51/42
[52] U.S. Cl. .................................... 562/600; 562/532; 562/535; 562/538; 562/593; 203/DIG. 21
[58] Field of Search ............... 562/600, 532, 535, 545, 562/538, 593; 203/DIG. 21

[56] References Cited

FOREIGN PATENT DOCUMENTS

| 1452566 | 8/1966 | France | 562/600 |
| 7610 | 3/1973 | Japan | 562/600 |
| 50-52021 | 5/1975 | Japan | 562/600 |
| 87309 | 8/1978 | Japan | 562/600 |
| 77643 | 5/1982 | Japan | 562/600 |

Primary Examiner—Werren B. Lane
Attorney, Agent, or Firm—Oblon, Spivak, McClelland, Maier & Neustadt

[57] ABSTRACT

Disclosed herein is a process for bringing methacrylic acid, which has been obtained by the catalytic oxidation of compound having 4 carbon atoms, into contact with a basic anion-exchange resin so as to remove byproduced dibasic acids and the like from the methacrylic acid and to purify the same.

4 Claims, No Drawings

PURIFICATION PROCESS OF METHACRYLIC ACID

BACKGROUND OF THE INVENTION (a) Field of the Invention

This invention relates to a process for removing dibasic acids, such as maleic acid and citraconic acid, contained methacrylic acid which has been obtained by subjecting a compound having 4 carbon atoms such as isobutylene, tertiary butanol, methacrolein or isobutyl aldehyde to catalytic oxidation with a molecular oxygen containing gas in the presence of steam.

(b) Description of the Prior Art

Methacrylic acid obtained by the catalytic oxidation of a compound having 4 carbon atoms, such as isobutylene, tertiary butanol, methacrolein or isobutyl aldehyde, with molecular oxygen in the presence of steam in a one-step or two-step reaction can be purified to a high-purity product by a usual rectification method such as extraction or distillation. It has however been difficult to achieve complete removal of impurities which are contained in trace amounts.

As these trace impurities, methacrylic acid has been found to contain dibasic acids such as maleic acid and citraconic acid besides protoanemonin, and monobasic acids such as acetic acid, propionic acid, isobutyric acid and acrylic acid byproduced upon synthesis of methacrylic acid. It has also been found that these dibasic acids accompany methacrylic acid due to sublimation, vapor-phase association and/or the like upon distillation and when methacrylic acid is employed in a polymerization reaction, they undergo crosslinking and the like to impair the polymerization properties of methacrylic acid.

It is therefore desirous to remove such dibasic acids completely in the purification step of methacrylic acid. Among these by-products, complete removal of dibasic acids and protoanemonin has been considerably difficult.

As a process for the removal of protoanemonin, Japanese Patent Laid-Open No. 44337/1984 discloses to add a bisulfite to an aqueous solution of methacrylic acid. Regarding a removal process of dibasic acids on the other hand, it is disclosed in Japanese Patent Laid-Open No. 99434/1983 that when an aqueous solution of methacrylic acid is extracted with a solvent subsequent to addition of a basic material thereto, aromatic carboxylic acids, maleic acid, polymers and tar-like matter are either modified or converted into their salts and their extraction is rendered more difficult, thereby making it possible to allow them to remain in the extraction residue and hence to achieve their removal. However, the present inventors are not aware of any publications in which dibasic acids such as maleic acid and citraconic acid are dealt with in detail.

According to the present inventors' experiences, it is necessary to increase the reflux ratio to an extremely high level or to increase the number of stages if one wants to separate and remove trace amounts of dibasic acids from methacrylic acid by distillation. Such an approach is however disadvantageous in both energy consumption and initial investment and moreover, is difficult to remove such impurities completely.

In addition, the present inventors tried to remove maleic acid and citraconic acid by the above-described process, i.e., by adding a basic material to methacrylic acid and then extracting the resultant mixture. Although a relatively high removal rate was achieved with respect to maleic acid, it was unable to lower the content of citraconic acid to any practically acceptable level. It was also confirmed that resultant salts of maleic acid and citraconic acid partly precipitated and dispersed in the extract and deposited in subsequent steps to close up outlet piping.

SUMMARY OF THE INVENTION

An object of this invention is to provide a process for the efficient removal of dibasic acids such as maleic acid and citraconic acid by-produced in the catalytic oxidation of a compound having 4 carbon atoms.

Another object of this invention is to provide a process for the efficient separation of citraconic acid from an aqueous solution which contains both maleic acid and citraconic acid.

The present inventors carried out an extensive research with a view toward developing a process for the removal of dibasic acids. As a result, it has been unexpectedly found that dibasic acids such as maleic acid and citraconic acid can be completely removed with extremely high selectivity by treating methacrylic acid, which has been obtained by the catalytic oxidation reaction of a compound having 4 carbon atoms, with a basic anion-exchange resin, leading to completion of the present invention.

In one aspect of this invention, there is thus provided a process for the purification of a solution containing methacrylic acid and obtained by subjecting a compound having 4 carbon atoms to catalytic oxidation with a molecular oxygen containing gas in the presence of steam, which comprises bringing the solution into contact with a basic anion-exchange resin.

In another aspect of this invention, there is also provided a process for separating citraconic acid from a basic anion-exchange resin with maleic acid and citraconic acid adsorbed thereon, which comprises applying maleic acid as an eluent to the basic anion-exchange resin so as to separate and recover citraconic acid, followed by application of a strong alkali to elute and recover maleic acid.

According to the first aspect of this invention, it is possible to convert a solution, which has been obtained by the catalytic oxidation of a compound having 4 carbon atoms with a molecular oxygen containing gas in the presence of steam, or methacrylic acid into methacrylic acid substantially free of dibasic acids by bringing the solution or methacrylic acid into contact with a basic anion-exchange resin. According to the second aspect of this invention, it is also feasible to achieve efficient removal of citraconic acid from an aqueous solution in which maleic acid and citraconic acid are contained.

The above and other objects, features and advantages of the present invention will become apparent from the following description and the appended claims.

DETAILED DESCRIPTION OF THE INVENTION

Preferred embodiments of this invention will hereinafter be described more specifically.

Methacrylic acid is usually obtained by catalytically oxidizing isobutylene, tertiary butanol, methacrolein or isobutyl aldehyde through a catalyst bed in either one or two stages. In such a process, methacrylic acid is purified by extracting methacrylic acid from its aqueous solution, which has been collected by cooling and condensing the resultant gaseous reaction mixture, with a solvent and then subjecting the thus-extracted methacrylic acid to a distillation process which consists of a step for the removal of the extractant, another step for the removal of low boiling-point fractions and a further step for the removal of high boiling-point fractions.

In the process of this invention, the methacrylic acid to be treated may be obtained from any one of the above-described steps. Namely, the present invention can be applied to all of the aqueous solution containing methacrylic acid and obtained from the cooling and condensing step of oxidation products, the extract obtained from the solvent extraction step, the condensed methacrylic acid solution obtained after the separation and recovery of the extractant, the medium purified methacrylic acid obtained from the removal step of the low boiling-point fractions, the methacrylic acid obtained in a substantially purified form from the removal step of the high boiling-point fractions, etc.

In the stage of each of the above-described steps, methacrylic acid may be esterified with methanol into methyl methacrylate. Since the esterification reaction is a equilibrium reaction, it is essential to incorporate a step for the recovery of unreacted methacrylic acid. The process of this invention can also be applied to methacrylic acid recovered in this step.

Maleic acid and citraconic acid are each mixed in an amount of 0.001–0.5 wt. % in such methacrylic acid, although their contents vary from one step to another.

No particular limitation is imposed on the type of a solvent to be used as a solvent for the extraction of methacrylic acid. In general, any solvents may be employed so long as the solvent is employed to recover methacrylic acid from aqueous solutions of methacrylic acid. Illustrative examples of the extractant include isobutane, butene-1, cis-butene-1, cis-butene-2, n-pentane, n-heptane, n-hexane, n-octane, cyclohexane, ethylbenzene, xylene, toluene, isopropyl acetate, methyl methacrylate, cyclohexanone, acetophenone, isophorone, methyl ethyl ketone and diisobutylene. They may be used either singly or in combination.

As exemplary basic anion-exchange resins useful in the practice of this invention, may be mentioned strongly basic anion-exchange resins typified by those containing the following exchange groups:

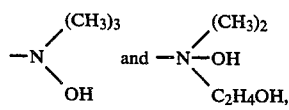

weakly basic anion-exchange resins represented by polyamines and those containing the exchange group —N(CH$_3$)$_2$, as well as medium basic anion-exchange resins represented by those containing the exchange group —CONH(CH$_2$)$_n$N(CH$_3$)2. As their resin forms, both porous resins and gel-type resins are usable. Basic anion-exchange resins for non-aqueous solutions are preferred especially when methacrylic acid is treated in a form other than its aqueous solution.

Regarding the manner of contact between the methacrylic acid containing solution and the basic anion-exchange resin, both batchwise and continuous methods may be employed without any problem. For industrial applications, the continuous method is however more advantageous. When the methacrylic acid containing solution is continuously brought into contact with the basic anion-exchange resin, it is possible to obtain methacrylic acid containing maleic acid and citraconic acid at concentrations below the lower detection limit of 1 ppm, namely, in a form substantially free of maleic acid and citraconic acid by causing a solution of the methacrylic acid, which is maintained at a prescribed temperature, to pass at a constant flow velocity through a column packed with a basic anion-exchange resin.

It is preferable to conduct the operation within a temperature range of 10°–60° C., notably 25°–40° C. If the temperature is too low, there is a danger that methacrylic acid would precipitate as crystals. Any excessively high temperatures are not preferable from the viewpoints of the heat resistance of the ion-exchange resin and possible polymerization of methacrylic acid. It is preferable to conduct the operation at a space velocity of 0.2–20 l/lhr, especially, 5–20 l/lhr when the total content of dibasic acids in methacrylic acid is 0.002–0.01 wt. % or at 0.2–5 l/lhr when the total content of dibasic acids in methacrylic acid is 0.01–1.0 wt. %. If the space velocity is too low, more resin has to be provided at the beginning and this is certainly uneconomical from the viewpoint of the initial investment although use of such an excessively low space velocity can bring about an advantage that the frequency of regeneration of the resin is reduced. If the space velocity is too high, the removal rate of intended dibasic acids such as maleic acid and citraconic acid is lowered and the frequency of regeneration of the resin is increased, thereby requiring more regenerating reagents and producing more washing effluent. It is thus not preferable to use any space velocity outside the above-described ranges. By the way, a dilute solution of methacrylic acid which solution is produced in the regeneration step of the resin can be treated without any substantial loss by recycling it to the aqueous solution in the preceding step or the extraction or distillation step.

There is a process for advantageously effecting the treatment a solution, which has been obtained by the above-described catalytic oxidation and containing methacrylic acid, with the basic anion-exchange resin by esterifying a portion of the solution with methanol and reducing the contents of dibasic acids in the solution. Namely, by an investigation conducted by the present inventors, it has been found that the esterification rates of dibasic acids are far greater than that of methacrylic acid. By making use of this phenomenon, it is thus possible to achieve high degrees of esterification for dibasic acids without esterifying methacrylic acid to a high degree. It is hence possible to reduce the contents of dibasic acids significantly, for example, to 180 ppm or lower of maleic acid and 140 ppm or lower of citraconic acid in the reaction mixture obtained by the above-mentioned esterification. This process allows to obtain methacrylic acid in a purified form completely free of dibasic acids by means of an ion-exchange apparatus with a small ion-exchanging capacity and to reduce the frequency of regeneration of the ion-exchange resin, provided that methyl methacylate is distilled off in a distillation step, which is conducted under usual conditions for the removal of methyl methacrylate by distillation, and the resulting fraction containing unreacted methacrylic acid is subjected to an ion-exchange treatment.

As the eluent employed upon separation and recovery of the ion-exchanged maleic acid and citraconic acid and regeneration of the ion-exchange resin for its reutilization, an inorganic or organic acid having a dissociation constant greater than citraconic acid is used so as to elute the citraconic acid selectively. Use of maleic acid as an organic acid for the elution of the citraconic acid in the above process results in selective substitution of maleic acid for the citraconic acid ion-exchanged on the resin and hence elution of the citraconic acid, thereby making it possible to obtain an aqueous solution of citraconic acid which solution contains substantially no maleic acid. By changing the eluent from maleic acid to an inorganic or organic acid having a dissociation constant greater than maleic acid, such as hydrochloric acid, upon completion of the elution of the citracbnic acid, it is possible to obtain an aqueous solution of maleic acid which solution is substantially free of citraconic acid. This aqueous solution can therefore be repeatedly used as an eluent for citraconic acid. Alternatively, it may also be recovered as maleic acid. The resin which has been substituted by hydrochloric acid can be used repeatedly subsequent to its regeneration with caustic soda.

Although similar results can be obtained by using, in place of maleic acid, another organic acid having a dissociation constant greater than citraconic acid but smaller than maleic acid, use of such an additional organic acid results in admixture of the additional material to the system. Eventually, the additional material has to be separated from maleic acid. It is therefore not strongly recommended to use organic acids other than maleic acid.

When an inorganic acid is used on the other hand, an inorganic acid having a dissociation constant between those of maleic acid and citraconic acid, for example, phosphoric acid or phosphorous acid can selectively elute citraconic acid in a manner similar to maleic acid. If the recovery of maleic acid is not important, the resin can be generated with strong acid. In the case of an inorganic acid having a dissociation constant greater than maleic acid, for example, hydrochloric acid on the other hand, the selectivity toward citraconic acid drops. Such an inorganic acid cannot be used accordingly. As treatment conditions for the selective elution of citraconic acid, it is possible to employ the same conditions as those followed upon ion-exchange of maleic acid and citraconic acid.

Methacrylic acid can generally be obtained in the following manner from a solution obtained by bringing a methacrylic acid containing solution into contact with a basic anion-exchange resin in accordance with the process of this invention, although the manner of treatment of the solution differs depending on the type of the solution. When an aqueous solution of methacrylic acid is treated, methacrylic acid can be obtained by extracting or distilling the treated solution in a usual manner. Since no dibasic acids such as maleic acid and citraconic acid are practically contained in the treated solution, it is unnecessary to think of selective removal of these dibasic acids upon conducting its extraction. This provides a high degree of freedom upon selection of an extractant, thereby facilitating selection of a solvent providing a high distribution coefficient for methacrylic acid. When distillation is relied upon, it becomes unnecessary to increase the reflux ratio to an excessively high value or to increase the number of plates for the removal of dibasic acids such as maleic acid and citraconic acid. Similar effects can also be obtained by using a conventionally-known polymerization inhibitor such as phenothiazine, hydroquinone, methoxyhydroquinone, methylene blue or molecular oxygen upon conducting the above treatment, extraction and/or distillation.

The process of this invention has great advantages from the view points of energy consumption and initial investment and permits easy and complete removal of dibasic acids, such as maleic acid and citraconic acid, contained as inherent impurities in methacrylic acid obtained by the catalytic oxidation of a compound having 4 carbon atoms. It is accordingly possible to obtain, with ease and a high yield, methacrylic acid of quality equal to or higher than that produced from acetone cyanohydrin.

The present invention will hereinafter be described more specifically by the following Examples.

EXAMPLE 1

A column (20 mm across and 30 cm long) was packed with 50 cc of a weakly basic anion-exchange resin, "Amberlyst A-21" [trade name; exchange groups: —N=(CH$_3$)$_2$]. A 10 wt. % solution of methacrylic acid in methanol was caused to flow at a space velocity of 1 l/lhr through the column until methacrylic acid was traced in the passed solution, thereby bonding methacrylic acid on the resin. Methacrylic acid having a purity of 99.5 wt. %, which had been obtained by using tertiary butanol as a starting raw material and containing maleic acid and citraconic acid respectively at 620 ppm and 450 ppm, was then caused to flow at a space velocity of 3 l/lhr through the column. After the above-mentioned methanol had been purged out of the column, the concentrations of maleic acid and citraconic acid in the resultant treated solution were monitored by high-performance liquid chromatography (HPLC). The purified methacrylic acid was found to contain maleic acid and citraconic acid below their detection limits of 1 ppm respectively.

EXAMPLE 2

A test was carried out in the same manner as in Example 1 except for the use of a strongly basic anion-exchange resin, "Amberlyst A-26" [trade name; exchange groups:

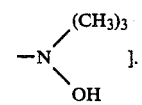

].

As a result, neither maleic acid nor citraconic acid was detected in the thus-obtained purified methacrylic acid.

COMPARATIVE EXAMPLE 1

Phenothiazine was added to a concentration of 100 ppm as a polymerization inhibitor in methacrylic acid which had been obtained by using tertiary butanol as a starting raw material and similar to Example 1, had a purity of 99.5 wt. % and contained maleic acid and citraconic acid at 620 ppm and 450 ppm respectively. The methacrylic acid was then distilled batchwise at a reflux ratio of 3 in an Aldhashaw-type glass column (30 mm across and 30 cm long; the number of theoretical plates: 7), thereby recovering methacrylic acid at a recovery rate of 90%.

The contents of maleic acid and citraconic acid in the thus-obtained methacrylic acid were 652 ppm and 486 ppm respectively.

EXAMPLE 3-6

Following the procedure of Example 1, a variety of aqueous solutions of methacrylic acid which solutions contained maleic acid and citraconic acid at various concentrations were caused to flow through the same column. Their space velocities were adjusted in accordance with their concentrations as shown in Table 1. Results are shown in Table 1.

TABLE 1

| Example | Before treatment (ppm) | | After treatment (ppm) | | Space velocity (l/lhr) |
|---|---|---|---|---|---|
| | Maleic acid | Citraconic acid | Maleic acid | Citraconic acid | |
| 3 | 50 | 10 | ≧1 | ≧1 | 10 |
| 4 | 10 | 50 | " | " | 10 |
| 5 | 180 | 150 | " | " | 5 |
| 6 | 2000 | 1000 | " | " | 1 |

EXAMPLE 7

An aqueous solution of methacrylic acid, which had been obtained by subjecting isobutylene, a starting raw material, to vapor-phase catalytic oxidation and then cooling, condensing and collecting the resultant gaseous reaction mixture, was subjected to sedimentation and filtration to separate the by-produced solid matter. The filtrate was thereafter caused to flow continuously at a flow velocity of 3 l/lhr (in terms of space velocity) at room temperature by a pump through a column (20 mm across and 30 cm long) packed with 50 cc of a strongly basic anion-exchange resin, "Amberlite IRA-400" [trade name; exchange groups:

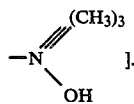

].

The concentrations of dibasic acids such as maleic acid and citraconic acid in the resultant solution were monitored by high-performance liquid chromatography (HPLC) while the concentrations of other components were monitored by gas chromatography (GC). The thus-monitored data became constant in about 2 hours. Their respective concentrations at the inlet and outlet of the column after that time point are shown in Table 2.

EXAMPLE 8

The treated solution obtained in Example 7 was subjected to an extraction treatment with n-hexane. The extract was distilled and rectified in an Aldhashaw column (30 mm across and 30 cm long; the number of theoretical plates: 7) to obtain methacrylic acid as a final product. The purity of the final product is given in Table 2.

COMPARATIVE EXAMPLE 2

Isobutylene, a starting raw material, was subjected to vapor-phase catalytic oxidation and the resultant gaseous reaction mixture was cooled, condensed and collected as an aqueous solution of methacrylic acid. After removing solid matter from the aqueous solution by sedimentation and filtration in the same manner as in Example 7, the filtrate was subjected to an extraction treatment in the same manner as in Example 8 to obtain methacrylic acid as a final product. The purity of the final product is given in Table 2.

EXAMPLE 9

Following the procedure of Example 7, the solution was continuously caused to flow at room temperature and a flow velocity of 4 l/lhr (in terms of space velocity) except that the resin was replaced by a weakly basic anion-exchange resin, "Lewatit MP-62" (trade name; exchange groups: —NR$_2$). The concentrations of maleic aid and citraconic acid at both inlet and outlet of the column were monitored. Analysis data by HPLC and GC subsequent to attainment of stable concentrations are shown in Table 2.

EXAMPLE 10

Treatment was conducted at various space velocities by using "Lewatit MP-62" in the same manner as in Example 9. Results are shown in Table 3. It is appreciated that the object was not achieved at the space velocity of 7 l/lhr.

TABLE 2

| Component (wt. %) | Example 7 | | Example 8 | Comp. Ex. 2 | Example 9 | |
|---|---|---|---|---|---|---|
| | Before treatment | After treatment | | | Before treatment | After treatment |
| Acetic acid | 1.73 | 1.65 | Undetected | Undetected | 1.73 | 1.75 |
| Propionic acid | 0.07 | 0.07 | 30 ppm | 32 ppm | 0.07 | 0.08 |
| Acrylic acid | 0.34 | 0.33 | 100 ppm | 110 ppm | 0.34 | 0.36 |
| Methacrylic acid | 24.03 | 24.10 | 99.88 | 99.78 | 24.03 | 24.32 |
| Maleic acid | 0.37 | ≧1 ppm | ≧1 ppm | 615 ppm | 0.37 | ≧1 ppm |
| Citraconic acid | 0.28 | ≧1 ppm | ≧1 ppm | 437 ppm | 0.28 | ≧1 ppm |
| Others | 1.25 | 1.10 | 150 ppm | 158 ppm | 1.25 | 1.30 |
| H$_2$O | 72.30 | 72.75 | 0.06 | 0.06 | 72.28 | 72.17 |
| Methoxyhydroquinone | 200 ppm | 210 ppm | 215 ppm | 203 ppm | 200 ppm | 182 ppm |

TABLE 3

| Space velocity (l/lhr) | 0.6 | 1 | 3 | 5 | 7 |
|---|---|---|---|---|---|
| Acetic acid | 1.70 | 1.65 | 1.73 | 1.62 | 1.80 |
| Propionic acid | 0.07 | 0.08 | 0.07 | 0.07 | 0.08 |
| Acrylic acid | 0.35 | 0.37 | 0.33 | 0.40 | 0.38 |
| Methacrylic acid | 24.30 | 24.17 | 24.52 | 24.27 | 24.52 |
| Maleic acid | ≧1 ppm | ≧1 ppm | ≧1 ppm | ≧1 ppm | ≧1 ppm |
| Citraconic acid | ≧1 ppm | ≧1 ppm | 1 ppm | 5 ppm | 30 ppm |
| Others | 1.10 | 1.42 | 1.21 | 1.36 | 1.29 |
| H$_2$O | 72.46 | 72.31 | 72.14 | 72.26 | 71.90 |

TABLE 3-continued

| Methoxyhydroquinone | 181 ppm | 193 ppm | 207 ppm | 203 ppm | 201 ppm |

(unit: wt. %)

EXAMPLE 11

Treatment was conducted under the same conditions as in Example 7 except that the resin was changed to a basic anion-exchange resin of a different kind. Results are shown in Table 4.

EXAMPLE 12

An extract containing methacrylic acid was extracted from an aqueous solution of methacrylic acid, which solution had been obtained by subjecting isobutylene as a starting raw material to vapor-phase catalytic oxidation and then cooling and condensing the resultant gaseous reaction mixture, by using xylene as an extractant. The extract was caused to flow at a space velocity of 4 l/lhr through a column (20 mm across and 30 cm long) packed with 50 cc of a weakly basic anion-exchange resin, "Amberlyst A-21" [trade mark; exchange groups: —N=(CH$_3$)$_2$], and the concentrations of maleic acid and citraconic acid in the thus-obtained treated solution were analyzed by high-performance chromatography (HPLC) while the concentrations of other components in the same solution were measured by gas chromatography. Results are shown in Table 5. As readily envisaged from Table 5, neither maleic acid nor citraconic acid were detected.

EXAMPLE 13

An experiment was conducted in the same manner as in Example 12 except for the use of methyl methacrylate as an extractant. Results are shown in Table 5.

EXAMPLE 14

Following the procedure of Example 12 except that the resin was changed to a strongly basic anion-exchange resin, "Amberlyst A-26" [trade name; exchange groups:

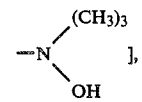

the extract was caused to room temperature and a space velocity of 4 l/lhr. Maleic acid and citraconic acid in the resultant treated solution were monitored. The HPLC analysis detected neither maleic acid nor citraconic acid after the treatment had been stabilized.

EXAMPLE 15

An experiment was conducted in the same manner as in Example 12 except that n-pentane was used as extractant. Results are shown in Table 5.

TABLE 4

| Anion-exchange resin Exchange groups | Neat solution | Styrene-base strongly basic anion-exchange resin —N(CH$_3$)$_2$·C$_2$H$_4$OH | Styrene-base strongly basic anion-exchange resin —N(CH$_3$)$_3$·OH | Styrene base weakly basic anion-exchange resin —N(CH$_3$)$_2$ | Acrylic medium-basic anion-exchange resin —CONH(CH$_2$)$_n$—N(CH$_3$)$_2$ |
|---|---|---|---|---|---|
| Trade name | | DIAION PA-312* | DIAION PA-418* | Amberlite IRA-94* | Amberlite IRA-68* |
| Acetic acid | 1.73 | 1.68 | 1.59 | 1.76 | 1.82 |
| Propionic acid | 0.07 | 0.07 | 0.08 | 0.07 | 1.82 |
| Acrylic acid | 0.34 | 0.38 | 0.41 | 0.32 | 0.36 |
| Methacrylic acid | 24.03 | 23.88 | 24.32 | 24.10 | 24.25 |
| Maleic acid | 0.37 | ≧1 ppm | ≧1 ppm | ≧1 ppm | ≧1 ppm |
| Citraconic acid | 0.28 | ≧1 ppm | ≧1 ppm | ≧1 ppm | ≧1 ppm |
| Others | 1.25 | 1.30 | 1.10 | 1.21 | 1.05 |
| H$_2$O | 72.28 | 72.67 | 72.48 | 72.51 | 72.43 |
| Methoxyhydroquinone | 200 ppm | 196 ppm | 206 ppm | 192 ppm | 189 ppm |

(unit: wt. %)

*Trade names.

TABLE 5

| | Example 12 | | Example 13 | | Example 15 | |
|---|---|---|---|---|---|---|
| Component (wt. %) | Before treatment | After treatment | Before treatment | After treatment | Before treatment | After treatment |
| Maleic acid | 284 ppm | ≧1 ppm | 0.42 | ≧1 ppm | 184 ppm | ≧1 ppm |
| Citraconic acid | 251 ppm | ≧1 ppm | 0.37 | ≧1 ppm | 145 ppm | ≧1 ppm |
| Methacrylic acid | 39.75 | 39.81 | 25.26 | 25.52 | 37.00 | 37.16 |
| Acrylic acid | 0.65 | 0.61 | 0.32 | 0.33 | 0.51 | 0.50 |
| Propionic acid | 0.16 | 0.17 | 0.11 | 0.12 | 0.16 | 0.15 |
| Acetic acid | 1.65 | 1.50 | 2.72 | 2.75 | 1.22 | 1.18 |
| Xylene | 55.11 | 55.29 | 68.90 | 69.37 | 58.90 | 58.81 |
| H$_2$O | 0.02 | 0.02 | 0.01 | 0.01 | 0.02 | 0.02 |
| Others | 2.57 | 2.58 | 1.87 | 1.90 | 2.14 | 2.16 |
| Methoxyhydroquinone | 225 ppm | 218 ppm | 250 ppm | 242 ppm | 216 ppm | 203 ppm |

EXAMPLE 16

After oxidizing isobutylene in two steps, the resultant methacrylic acid was substantially purified by the above-described extraction step, extractant recovery step, distillation step and the like. It contained maleic acid and citraconic acid at 225 ppm and 173 ppm respectively. After addition of methanol to the methacrylic acid, the resultant mixture was caused to flow under the conditions of a space velocity of 0.5 1/lhr and a temperature of 70° C. through an esterification column in which a strongly acidic cation-exchange resin was packed as a catalyst so that esterification of the mixture was performed. The thus-obtained reaction mixture had the following composition: 43.2 wt. % methyl methacrylate, 26.6 wt. % methacrylic acid, 21.8 wt. % methanol, 45 ppm maleic acid, 26 ppm citraconic acid and the remainder water. The reaction mixture was distilled to obtain a methacrylic acid fraction which containing maleic acid and citraconic acid at 164 ppm and 96 ppm respectively. This methacrylic acid fraction was caused to flow at a temperature of 30° C. and a flow velocity of 10 1/lhr (in terms of space velocity) through a column having an inner diameter of 20 mm and a length of 300 mm and packed with 50 ml of a weakly basic ion-exchange resin, "Amberlyst A-21" [trade name; exchange groups: $-N=(CH_3)_2$]. At the beginning of the treatment, methacrylic acid was also adsorbed on the resin along with maleic acid and citraconic acid. Thereafter, the thus-adsorbed methacrylic acid was gradually substituted by maleic acid and citraconic acid, thereby obtaining purified maleic acid which was practically free of maleic acid and citraconic acid. The thus-treated fraction was analyzed by high-performance liquid chromatography. As a result, the contents of both acids were found to be below the detection limit of 1 ppm. The recovery rate of methacrylic acid in the purified methacrylic acid obtained until citraconic acid started accompanying the purified acrylic acid was 99.2 mole %.

EXAMPLE 17

In a glass column (20 mm across and 30 cm long), 50 cc of "Lewatit MP-62" (trade name for a weakly basic anion-exchange resin; exchange groups: $-NR_2$) was packed. At a space velocity of 3 1/lhr, an aqueous solution of methacrylic acid (30.5 parts methacrylic acid, 1.5 parts maleic acid, 0.8 part citraconic acid, and 67.2 parts water) was caused to flow through the glass column. All the components were monitored with an interval of 10 minutes. Maleic acid and citraconic acid remained both below 2 ppm until the 60th minute. Upon an elapsed time of 70 minutes, the concentration of citraconic acid jumped to 20 ppm, in other words, citraconic acid was found to flow out through the column. The feeding of the aqueous solution was stopped at that point and instead, a 1 wt. % aqueous solution of maleic acid was caused to flow at a space velocity of 2 1/lhr through the column with a view toward effecting elution of citraconic acid. The concentrations of maleic acid and citraconic acid were monitored. Upon an elapsed time of 70 minutes, maleic acid was found to flow out through the column and the feeding of the aqueous solution was stopped. The volume of the thus-obtained citraconic acid containing eluate was 116 cc and the concentration of citraconic acid was 1.1 wt. %.

What is claimed is:

1. A process for the purification of a solution of methacrylic acid, said methacrylic acid being prepared by subjecting a compound selected from the group consisting of isobutylene, tertiary butanol, methacrolein and isobutyl aldehyde to catalytic oxidation with a molecular oxygen-containing gas in the presence of steam, which comprises;

extracting said solution of methacrylic acid containing maleic acid and citraconic acid with an organic solvent;

contacting said extract or methacrylic acid obtained by distilling the organic solvent from the extract, with a basic anion-exchange resin, thereby removing maleic acid and citraconic acid from said solution of methacrylic acid;

recovering citraconic acid by applying maleic acid as an eluent to the citraconic acid-maleic acid containing basic anion-exchange resin obtained from said contact step; and then contacting the eluted resin obtained with a strong alkali, thereby eluting maleic acid from the resin and regenerating the resin for reutilization.

2. The process as claimed in claim 1, wherein said organic solvent is isobutane, butene-1, cis-butene-2, n-pentane, n-heptane, n-hexane, n-octane, cyclohexanone, ethylbenzene, xylene, toluene or methyl ethyl ketone.

3. A process for separating citraconic acid from a basic anion-exchange resin having maleic acid and citraconic acid adsorbed thereon, which comprises:

applying maleic acid as an eluent to said basic anion-exchange resin thereby eluting and recovering citraconic acid from said resin; and treating the resin with a strong acid thereby eluting and recovering maleic acid from the anion-exchange resin.

4. The process as claimed in claim 3, further comprising:

after treating said resin with a strong acid, further contacting said resin with a strong alkali, thereby regenerating the resin for reutilization.

* * * * *